United States Patent
Gottsmann et al.

(10) Patent No.: US 6,342,043 B1
(45) Date of Patent: Jan. 29, 2002

(54) SWIVELLING FRACTURE ORTHOSIS

(75) Inventors: Gert Gottsmann, München; Paul Prall, Petershausen; Elke Petra, Anzing, all of (DE)

(73) Assignee: Gert . Gottsmann, München (DE)

(*) Notice: Subject to any disclaimer, the term of this patent is extended or adjusted under 35 U.S.C. 154(b) by 0 days.

(21) Appl. No.: 09/423,480

(22) PCT Filed: May 4, 1998

(86) PCT No.: PCT/DE98/01231

§ 371 Date: Dec. 10, 1999

§ 102(e) Date: Dec. 10, 1999

(87) PCT Pub. No.: WO98/49979

PCT Pub. Date: Nov. 12, 1998

(30) Foreign Application Priority Data

May 7, 1997 (DE) .......................... 197 19 140

(51) Int. Cl.$^7$ .................................. A61F 5/00
(52) U.S. Cl. ................ 602/12; 602/5; 602/16; 602/20
(58) Field of Search .................. 602/5, 6, 9, 12, 602/16, 20, 21, 22, 23, 24, 25, 26, 27, 60–65, 78

(56) References Cited

U.S. PATENT DOCUMENTS

| 1,389,525 A | 8/1921 | Mosby |
| 2,667,868 A | 2/1954 | Smyth |
| 3,232,289 A | 2/1966 | Zimmerman |
| 4,576,153 A | 3/1986 | Zagorski et al. |

FOREIGN PATENT DOCUMENTS

| DE | 207 893 | 3/1909 |
| EP | 190 543 | 8/1986 |
| GB | 2 108 849 | 5/1983 |

*Primary Examiner*—Kim M. Lewis
(74) *Attorney, Agent, or Firm*—Cohen, Pontani, Lieberman & Pavane

(57) ABSTRACT

A rolling fracture orthesis, including a shell that is roll-flexible in a circumferential direction to surround a limb to be supported, the shell having adjacent bend-resistant strips that are pivotably interconnected and arranged parallel to each other in a longitudinal direction. Hook and pile fastener tapes are arranged to hold the strips together. A breathable, skin-compatible material is applied to only an inner side of the strips. The hook and pile fastener tapes are passed completely around an outer circumference of the shell always in a same direction of application.

26 Claims, 4 Drawing Sheets

FIG. 3
FIG. 5
FIG. 4
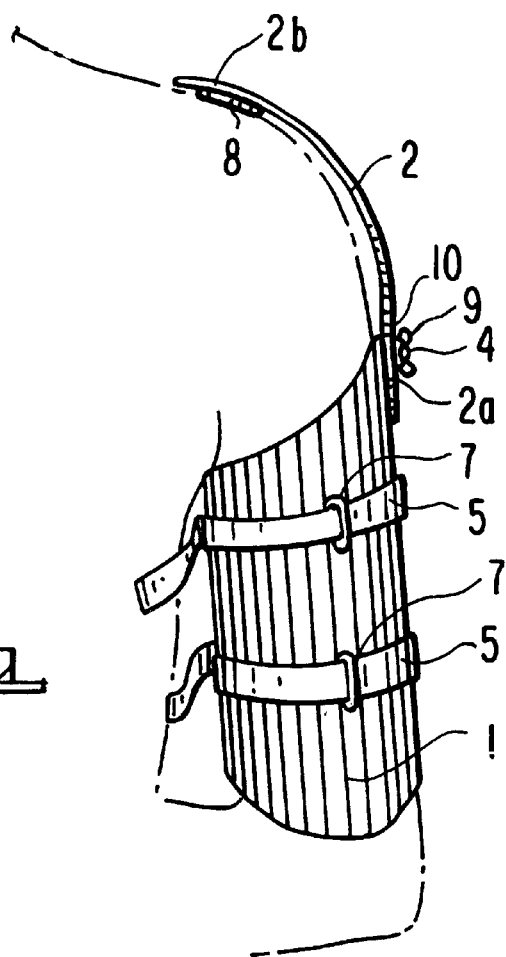
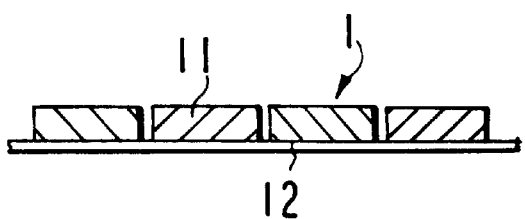
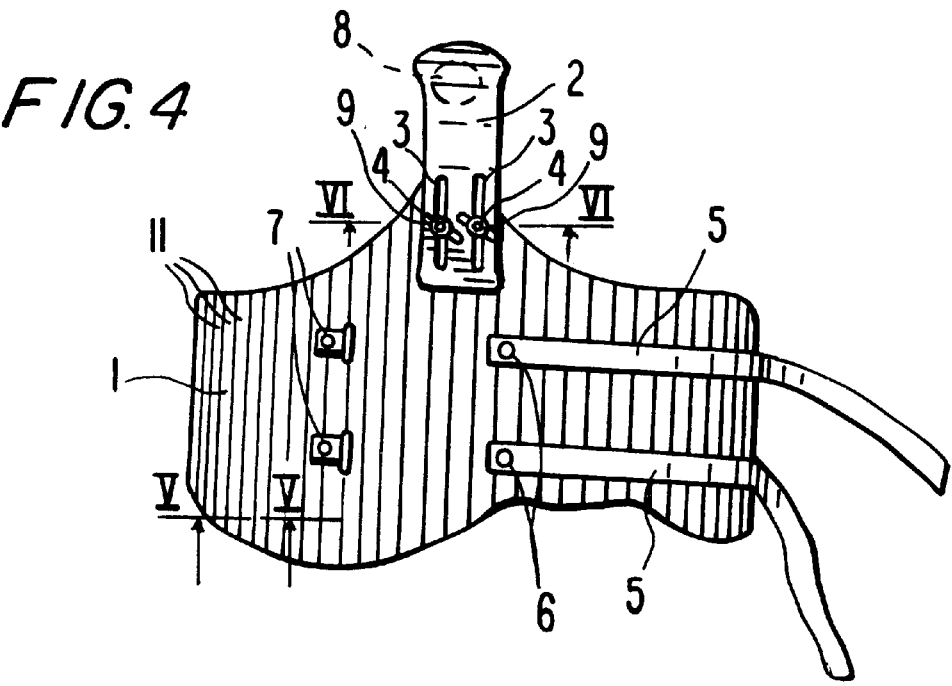

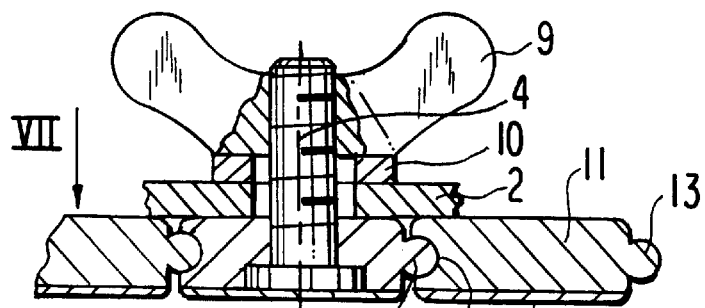
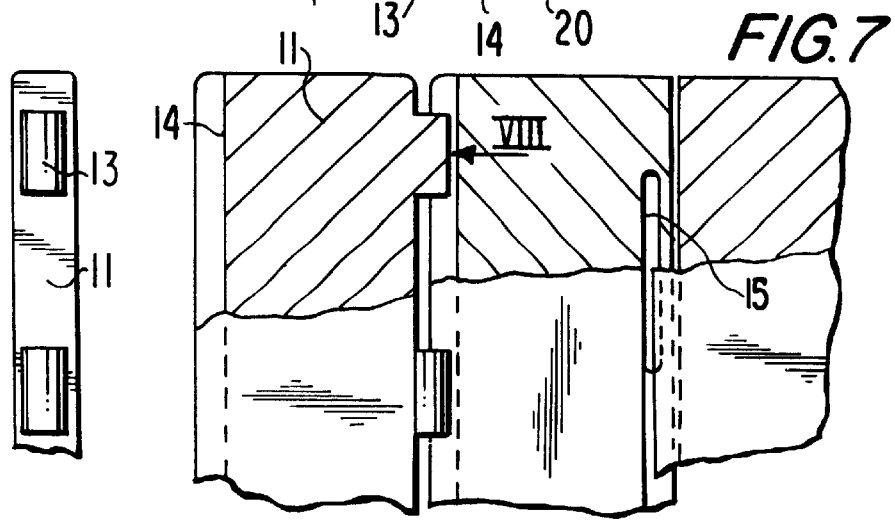
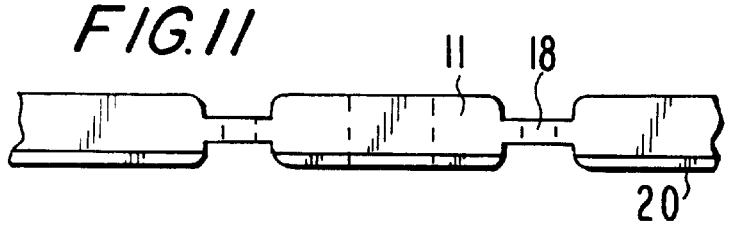
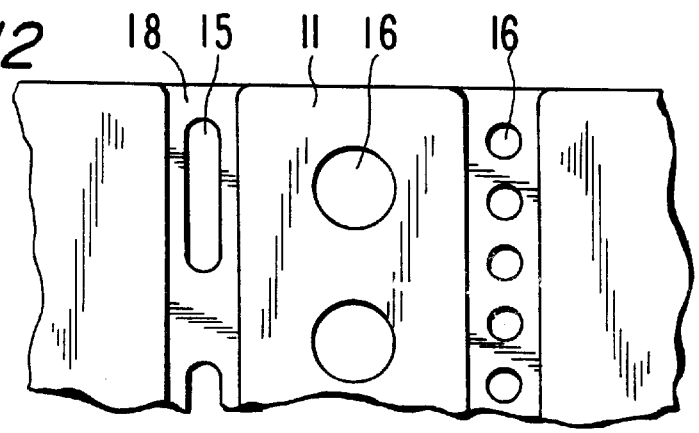

SWIVELLING FRACTURE ORTHOSIS

BACKGROUND OF THE INVENTION

1. Field of the Invention

The invention relates to a rolling fracture orthesis, especially a humerus fracture orthesis (upper arm orthesis), such as is for example applied after a fracture between the proximal and distal third of the humerus shaft, either on the day of the injury or during subsequent treatment after the initial immobilization dressing has been removed.

2. Discussed of the Prior Art

Ortheses of this type are, for example, described in the leaflet 2/90 "MANUAL for the functional conservative treatment of fractures with the Miami fracture orthesis system according to Sarmiento Latta" from the company Th ämert, 30938 Burgwedel. The humerus fracture orthesis presented and described therein, the Miami system, comprises two gutter-shaped half shells that enclose the upper arm between the axilla and elbow and are held together by hook and pile fastener tapes together with plastic loops. These half shells are prepared from perforated, smooth, waterproof plastic and are applied over a double cotton tube previously pulled on from the elbow to the axilla. When applying, the anterior shell is first applied, then the posterior shell, after which two hook and pile fastener tapes set at a distance from each other along one long side are passed through plastic loops on the anterior shell and are then passed through other plastic loops attached at suitable intervals along the second long side of the posterior shell and are turned back by 180° and fastened. The tapes are thus firmly fixed on only one side so that, apart from painful drawing, displacement of the orthesis can be caused. In addition, the orthesis fixed in this way can displace along its longitudinal direction on the underlying cotton tube so that it slips downward, its seating becomes loose and an obstacle to bending the elbow is created. The orthesis then has to be constantly undone and pushed up to the correct position and the tapes fastened again, which can be painful and also may have an adverse effect on the fracture. In addition, the known orthesis provides no control over the movement of the upper arm. A previous plaster cast (immobilization dressing) that is also applied after the fracture possesses a cap that leads over the shoulder. When the patient comes up against the cap during movement of his arm, he knows that he must immediately lower his arm.

In this respect it is to be noted that humerus fracture ortheses, which are increasingly being applied in accident surgery departments and clinics to fractures not surgically treated, have to be manufactured and be available in three or four sizes (S, M, L and XL) and also in versions for the left and right arm. The storage space required for the voluminous shells or hollow bodies in the assembled state is certainly very great when it is considered that a total of eight models (four sizes, each for right and left) have to be stocked.

This leaflet also presents a tibia fracture orthesis (lower leg orthesis) which has a heel cap for fixed positioning of the tibia orthesis. After prior determination of position, the heel cap is fastened to the posterior orthesis shell by non-detachable adhesive strips. If this fixation is not undertaken correctly, readjustment with respect to height of the orthesis or cap angle is no longer possible.

U.S. Pat. No. 4,863,968 also presents an ulna fracture orthesis (forearm orthesis) in which an L-shaped moulded hand limitation cap is attached to the lower shell and ensures that the hand is held approximately perpendicular to the forearm. This hand limitation cap is fixed to the lower shell in the definitive position by ratchet rivets which provide an initial adjustment but do not allow subsequent readjustment.

A device for immobilization and provision of heat or cold to a bodily joint is known from U.S. Pat. No. 4,753,240, comprising a flexible textile cut-out that is placed around the arm or leg and is held together by hook and pile fasteners facing each other on the non-overlapping ends. This shell is very soft not only in the transverse direction but also in the longitudinal direction, except for a thin, central longitudinal segment, e.g. at the heel or shoulder, where an adapted, angled shape can, if required, be applied by the insertion of inelastic, bendable metal rods. A firm, even hold with great longitudinal rigidity that must be ensured on the day of injury or as a follow-up treatment can therefore not be achieved with this known device.

U.S. Pat. No. 4,492,225 describes neck supports and arm splints formed from multilayered material. Thus, for example, for an arm or leg splint some inelastic, easily deformable metal strips, e.g. thin aluminum strips, are applied to the inside of an external hard foam plate and are covered with a thick internal cushioning layer of foam to give a material thickness of at least 25 mm. In addition, the relatively wide-apart, broad margins of the applied supports are held together only by a few short hook and pile fasteners so that in all and not least because of the pliant inner padding about 20 mm thick, adequate longitudinal stability cannot be achieved with these known supports.

A portable buttock and leg splint is described in U.S. Pat. No. 4,580,555 that comprises a long, thin cut-out composed of two layers of Nylon material into which a row of parallel, flat rods are sown in longitudinal pockets. When applying, the patient sits on the orthesis and the two relatively short side margins that do not cover t upper surface of the leg are drawn up and, by means of upper tension bands, fix the leg to the base. Apart from the fact that the flat rods used appear to be relatively broad and are present in only one part of the support surface, the fact that the support incompletely surrounds a limb means that its use as an upper arm orthesis, for example, cannot be sensibly achieved.

U.S. Pat. No. 2,138,975 describes a surgical splint composed of several units, that can be optionally lined up against each other and, through double joints that can be fixed in any position, can be pushed together to form a solid, inflexible plate or folded to form a small packet. Due to the great width of the parts, this known splint cannot be used for a fracture orthesis with a shell that is bend-resistant in the longitudinal direction.

An inflatable arm splint is described in U.S. Pat. No. 1,101,076, composed of a flat, foldable part with long edges that, when wrapped around an injured leg for example, fit together like a tongue-and-groove joint and are held together by a clip to form a pneumatic cuff. This inflatable emergency splint can be used only for a short time until a plaster cast is applied and is not for longer use, especially as it does not ensure adequate longitudinal stability.

A dressing splint is known from DE-GM 1,750,875 with longitudinal metal bars connected by cross-pins and comprising elastic, mat-shaped plastic parts bearing large gaps, and which can be fitted together if required. This elastic dressing splint is applied directly to the limb requiring support, and is held in place by winding round with a bandage. This known dressing splint is not suitable as an orthesis that patients can apply themselves if necessary and that exhibits adequate longitudinal rigidity.

A splint is described in U.S. Pat. No. 2,273,028 that is composed of corrugated, perforated plastic material that is cut out as required, applied and fitted with appropriate bandages for fixation. A provisional splint made from this material cannot be worn for long periods and cannot be re-applied by patients themselves when necessary.

Finally, U.S. Pat. No. 1,964,694 discloses a surgical splint composed of several rigid, perforated shell parts, whereby the shells are aligned together in a transversely adjustable manner by means of a rectangular angle unit together with elongated holes and wing-nuts. This known orthesis cannot be used as a complete orthesis embracing the entire circumference of a limb and providing optimum immobilization.

SUMMARY OF THE INVENTION

The object of the invention is therefore to provide a rolling fracture orthesis, especially a humerus fracture orthesis of the above type, whereby with a simple construction it is possible to obtain reliable, actively breathing immobilization of the limb segment by only two orthesis designs (left and right) that cover all sizes and can be tightly rolled up, and that can be applied and worn easily, with precise positioning and resistant to displacement, with optimal readjustment of position.

Accordingly, the roll-flexible orthesis is formed of single shell that is composed of several adjacent bend-resistant strips that are pivotably interconnected and arranged parallel to each other in the longitudinal direction, whereby a breathable, skin-compatible material such as cotton cloth is applied, e.g. by adhesive, only to the inside of the strip, and the hook and pile fastener tapes that fully encompasses the outer circumference of the overlapping shell to hold it together in the applied state always run in the same direction as the application or pull. A rolling shell, i.e. a flexible "rolling humerus fracture orthesis" that is bend-resistant in the longitudinal direction and can be rolled up tightly is created in this way. In the removed state, this rolling shell can be laid flat on a support such as a table and/or can be rolled up tightly into a roll for packing in a box or any container for clearing away and thereby saving a great deal of room. Because the rolling shell can be easily adjusted to any arm thickness and can be simply applied to any arm no matter how thin or thick, whereby its two long ends then merely overlap to a greater or lesser extent, it is possible to provide the inventive orthesis in just a single size, i.e. in only two models, namely a left model and a right model. Instead of the previous eight models, now two models are sufficient. This thus provides the great advantage of reducing the space and the number of units required, especially with regard to storage and preparation. The application of the inventive rolling orthesis is also extremely simple since essentially its middle is applied along the arm and the two ends are wrapped firmly around the arm and overlap, after which the rolling shell is fixed to the arm by means of hook and pile fastener tapes, preferably two tapes. In addition, because the hook and pile fastener tapes are passed completely around the outer circumference of ted, applied rolling shell, always in the same direction of application or pull, without change of direction, gentle application and fixation without jerky pulling back or lashing down is achieved with these tapes. In additional advantageous designs, even greater reliability of application and wearing is achieved by means of at least one metal or plastic loop and one or more hook and pile fastening points around the circumference. Instead of the relatively cumbersome guide loops, just one or more peripheral-humps, burls, etc., each arranged in pairs, can allow the positional fixation or guidance of the tapes around the shell.

It is advantageous if the strips of the rolling shell are made of plastic, wood or metal, or a combination of these materials. The choice of material can be made individually depending on the criteria considered most important, such as price, environmental friendliness, etc.

The strips are preferably made from hard material such as hard plastic and are about 9 mm wide and about 3 mm thick.

It is of further advantage if an air-permeable, tear-resistant, flexible support material such as cotton-canvas, woollen cloth or other textile is applied or attached by adhesive to one side of the strips. The textile support material plays two roles, the first being to act as a breathable, non-slip and skin-compatible internal liner so that prior application of a cotton tube to the upper arm is no longer necessary. In addition, the support material simultaneously acts as a pivot or joint element between the bend-resistant strips and allows the rolling shell formed in this way to be rolled up as a tight roll with the support material on the inside of the roll. The small gaps between the strips also allow exchange of air through the textile support material and this inhibits sweating. The cotton tubes previously used under plastic shells are not needed since the material (cloth) from which the flexible rolling shell is made is skin-compatible.

In another embodiment the strips may be joined together directly by joints, i.e. without intermediate foreign material, whereby each strip exhibits on its two long-thin sides a joint element, thus a shaft part and a joint socket or joint cup part. These parts may be of various designs, whereby any effective known design of known joint connections between corresponding strips, rods, etc. may be used, especially roller shutter, venetian blind and roll-fronted cupboard designs, etc. In addition, the essentially cylindrical joint socket and the joint shaft that fits into this socket in a swivellable manner extend along the entire length of the strips or boards, whereby the joint shaft may, depending on the strength requirement, be in one piece or be divided into several parts at intervals. In all cases it is important that the strips can swivel sufficiently between each other and that the strips are held together adequately in the transverse or tangential direction.

The strips may be prepared from solid material or from the hollow box forms with internal stiffening ribs known in the roller-shutter technique. In the latter design with internally stiffened hollow box forms, the joint shaft is formed as a hook that engages in a swivellable manner in the narrow-sided joint socket of the adjacent strip and can be displaced in the longitudinal direction (by known means can be locked from longitudinal movement after fitting together) and also can be slightly displaced inside the socket in the tangential or transverse direction with some play. Apart from a relatively recent method of manufacture in the case of plastic material preparation, e.g. by extrusion, very great further advantage is achieved in that with the rolling shell already applied, the shell can be drawn somewhat closer by the tapes since the individual strips may be pushed close or drawn further apart at the joints. If, after applying and fastening the shell it is found that it is sitting a little too loosely, it is thus not necessary to remove the entire shell but only necessary to release the tapes a little, e.g. to the next fastening point, and then draw them rather more firmly over the periphery so that the strips close up and the circumference is reduced overall and the rolling shell achieves a firmer seating. A firm, constrictive seating that could stop the blood circulation in the arm can be easily and quickly adjusted by partial loosening and then looser fastening of the tapes without the patient requiring special additional help or even without having to reapply the orthesis.

In another embodiment, the inventive rolling shell may be prepared in one piece practically from the same piece of material, whereby the strips and the interconnecting joints are produced by arranging thinner bending bridges between the strips.

These bending bridges between the strips may be thinner interconnecting bridges located either at the inner base of the strips or higher up at mid-height between the strips. If the bridges between the strips are at mid-height it is of great advantage that a one-piece, roll-flexible and simultaneously longitudinally rigid part is obtained that exhibits the same good rolling or flexibility properties on both sides. In this way the same shell shape can be cut out for preparation of the left and right models, whereby only the subsequent application or attachment of the tapes, fixing points and loops determines whether it is a left or right model. However, this can also be determined at a later stage by applying adhesive strips to suitable points marked for right or left so that, if necessary, a left or right orthesis can be prepared on site with a little manipulation. As a result, with this design only a single embodiment is required instead of the previous eight embodiments. It should be noted that this is very advantageous both in terms of cost and in terms of storage, which itself also has a noticeable effect on costs.

The inventive rolling orthesis can finally also be produced in a one-piece form such that the bending bridges between the strips are formed as arches curving outwards, whereby the strips are approximately as thick as the arches. In all, a roughly corrugated sheet form is obtained with the corresponding properties and certainly good flexibility in the transverse direction and great rigidity in the longitudinal direction.

In all these embodiments with direct connection between the strips, i.e. without textile support material, as already noted a breathable and skin-compatible inner lining, preferably of textile material, is applied to the inside of the bridges. Holes and/or slits should also be provided in the bridges or connecting parts for adequate ventilation. Good air circulation can be achieved through the hollow channels formed under the bridges in an embodiment with bridges raised above the application surface and additionally presenting slits or holes.

It is of particular advantage if, in the embodiment of the orthesis as a humerus fracture orthesis, a shoulder retention cap which is essentially L-shaped or adapted to the shoulder-arm outline is secured to the outer part of the rolling shell applied to the arm, and its position can be adjusted. This shoulder retention cap is secured essentially in the middle of the upper shell zone so that it follows the outer contour of the arm, essentially vertically at first, and then runs like a cap over the shoulder so that its upper section is essentially vertically supported on the shoulder. This prevents the orthesis slipping down since there is always vertical support. There is also additional control of the movement of the upper arm by the patient.

The use of orthesis retention caps or elements to counteract longitudinal displacement of ortheses is certainly known. However, after prior adjustment to the corresponding longitudinal position they are definitively secured so that any longitudinal displacement or swivelling of the cap that is subsequently required is no longer possible. The patient has to make do with the position of the orthesis once it is determined, even if this position is not optimal.

The inventive shoulder retention cap advantageously exhibits a long vertical guide arm and a short roughly horizontal supporting arm that run into each other in an arch shape. At its outer end the supporting arm exhibits a cushion formed as a round foam rubber pad or a long strip pad over the entire longitudinal strip leading from the shoulder arch. The round pad is preferred since it provides more accurate vertical support.

The longer guide arm of the shoulder retention cap is secured by its lower end section that is shaped to fit the shell and lies overlapping on the shell; it is secured in such a way that it can be shifted longitudinally and can be swivelled vertically/longitudinally. Where required, this allows pre-adjustment or re-adjustment of the orthesis position relative to the shoulder. Because the shoulder retention cap is easily swivelled, optimal support can also be achieved on the shoulder since the position of the shoulder varies from person to person depending on their posture, i.e. depending on how curved the back or shoulders are.

The displacement and/or swivelling capacity of the shoulder retention cap over its guide arm on the shell is preferentially achieved in that two parallel longitudinal guide slots are present on the lower end section of the guide arm overlapping the shell and are each traversed perpendicularly by a bolt that is firmly anchored in the shell. The connection can be undone or secured quickly by means of wing nuts or milled nuts that fit onto these bolts, i.e. nuts that can be operated without tools but by hand quickly and without particular force. After successfully applying the orthesis, by slightly loosening the screw connections the patients can thus themselves shift the shoulder retention cap in the longitudinal direction and/or swivel it slightly further forward or back from the vertical position so that optimal support and very good wearing comfort are achieved with optimal seating and wearing properties of the orthesis.

It is also advantageous if the shoulder retention cap is gutter-shaped with essentially the same radius of curvature as the shell in the applied state or is slightly transversally elastic to allow tangential deformation when applying and removing the orthesis, and if it is made of essentially the same material as the strips of the rolling shell and preferably of waterproof plastic fitted with air holes.

Pleasant wearing properties are achieved if the upper end of the support arm of the shoulder retention cap is rounded off as a semi-circle and at the same time the round pad follows the contours to some degree.

The invention is explained in more detail below on the basis of several embodiment examples and with reference to the drawings.

BRIEF DESCRIPTION OF THE DRAWINGS

The figures show:

FIG. 3: a posterior view of the orthesis according to FIGS. 1 and 2;

FIG. 4: a plan view of an orthesis according to FIGS. 1–3 in the laid-out, flat, unrolled state, in the embodiment for the right arm;

FIG. 5: a partial section through line V—V in FIG. 4;

FIG. 6: a partial section through line VI—VI in FIG. 4 in a further embodiment (roller-shutter design);

FIG. 7: a partial plan view of a partial section at arrow VII in FIG. 6;

FIG. 8: a view of the narrow longitudinal side of a rolling shell strip at arrow VIII in FIG. 7;

FIG. 11: a partial view in the longitudinal direction of a rolling orthesis in a further embodiment with straight bending bridges;

FIG. 12: a plan view of the embodiment according to FIG. 11;

DETAILED DESCRIPTION OF THE PREFERRED EMBODIMENTS

Figure 1:
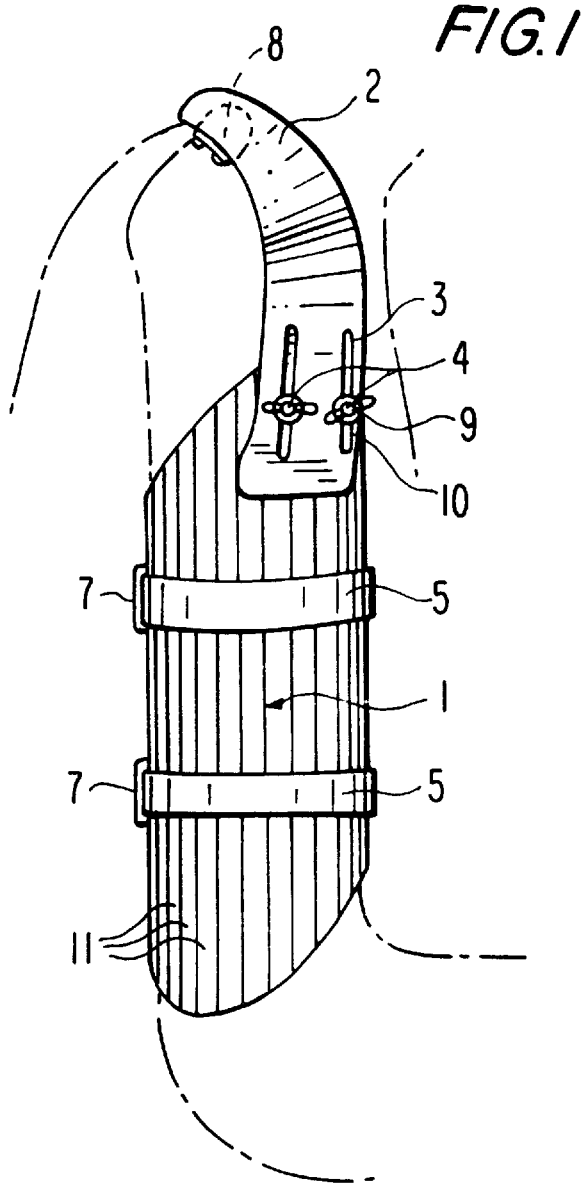
FIG. 1: a lateral view of an applied rolling orthesis with shoulder retention cap.
Figure 2:
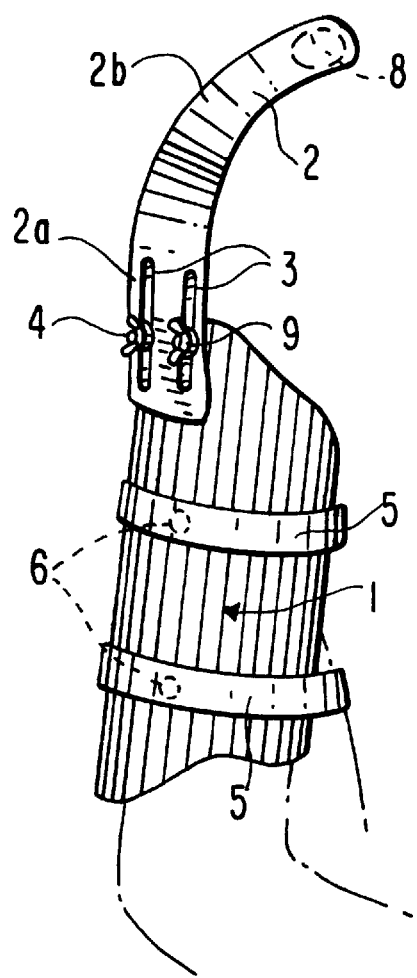
FIG. 2: an anterior perspective view of an orthesis according to FIG. 1.

As illustrated in FIGS. 1–4, in which the inventive orthesis is shown in an embodiment as a humerus fracture orthesis, this orthesis comprises a single, roll-flexible shell 1 (rolling shell) which is applied overlapping around the upper arm and is fixed in place with two hook and pile fastener tapes 5. The hook and pile fastener tapes are thereby held in position on the rolling shell 1 by means of hook and pile fastening points 6 and plastic or metal guide loops 7. The tapes 5 thereby always pass in the same peripheral direction around the applied rolling shell 1 and are fixed at their outer end to the corresponding upper hook and pile fastening point at the start of the tape.

As can be seen particularly in FIG. 4, in which the vi orthesis is illustrated as an embodiment of the orthesis for a right arm, the rolling shell 1 shows various cutouts at the upper and lower edges that allow optimal seating with regard to the axilla and elbow. The hook and pile fastener tapes 5 are secured to one side or half of the rolling shell 1 and on their upper side they each show a hook and pile fastening point 6 on their end that is firmly secured to the rolling shell. On the other half of the shell are the guide loops 7 through which the tapes 5 are passed to be fixed in position after applying the shell 1.

As can be seen from FIGS. 1–4 and particularly from FIG. 4, a shoulder retention cap 2 is secured in the upper zone of the rolling shell 1 and certainly essentially in its middle, this cap being essentially L-shaped and approximately follows the shape and curvature of the shoulder-arm line. It is composed of a guide arm 2a running approximately vertically in the applied state and a horizontal upper support arm 2b that merge into each other via an intermediate curved part.

At the lower end of the guide arm 2a that overlaps the shell are two parallel guide slots 3 running vertically or longitudinally, through each of which passes a bolt 4 that is secured to and projects horizontally from the shell 1. Onto each of these bolts 4 fits a wing-nut 9, under which is a washer 10, as can be seen more precisely in FIG. 10, in order to provide good support for the nut.

Underneath the upper, rounded end of the support arm 2b is a round pad, e.g. of foam rubber or formed as a foam rubber-filled cushion 8. This ensures comfortable vertical support of the orthesis virtually at one point.

As can be seen from FIGS. 1–5, especially FIG. 5, the rolling shell 1 of the inventive orthesis can be composed of a flexible support material 12 that, for example, may be a firm cotton-canvas material. On this support material 12 are applied, e.g. by adhesive, plank-shaped, bend-resistant strips 11 close together in parallel to form the shape of the flexible rolling shell 1. The thin intermediate gaps between the strips 11 allow good air exchange and inhibit sweating.

In the embodiment illustrated in FIGS. 6–8, the strips 11 are connected together directly by joints, whereby joint shafts 13 are provided on one of the long thin sides and engage in the joint sockets 14 or housing on the other long thin side. The shafts 13 and housings or sockets 14 are essentially cylindrical in form in this embodiment and, as may be seen from FIGS. 7 and 8, can be formed as one continuous piece or be divided into several pieces. A breathable, skin-compatible inner lining 20 is applied, e.g. by adhesive, to the inner side of each strip 11.

From FIG. 6 it can also be seen that, for example, the shoulder retention cap 2 is secured to the rolling shell 1 by bolts 4 and nuts 9, here wing nuts, with underlying washers 10.

Figure 9:
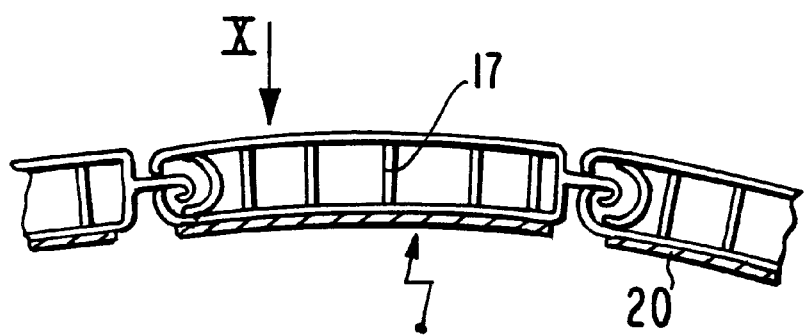
FIG. 9: a partial view in the longitudinal direction of a rolling shell in a further embodiment.
Figure 10:
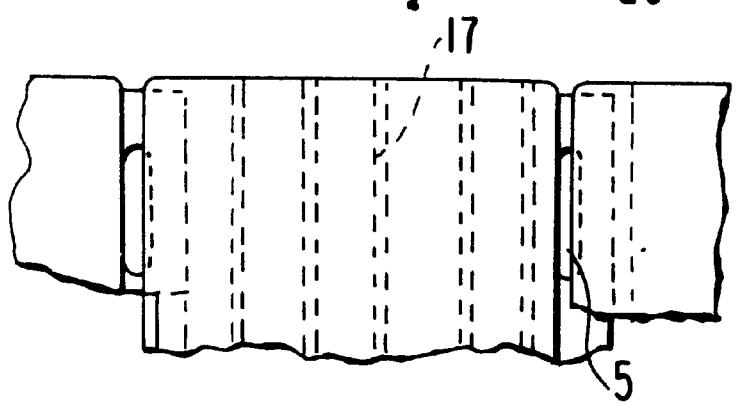
FIG. 10: a plan view at arrow X in FIG. 9.

In the embodiment according to FIGS. 9 and 10, the strips 11 are formed as hollow boxes with internal strengthening ribs 17. The joint shafts 13 are formed as hooks that engage in the housing openings or joint sockets 14 in such a way that these latter tightly enclose the thin fastening bridges of the hooks, whereby the hook length is adapted to the depth of the joint socket so that at least slight tangential or transverse to and fro movement of the strips is possible through their swivelling connections. It can be seen from FIG. 9 that the strips 11 may exhibit a curvature matching the circumference. FIG. 10 shows that ventilation slits 15 are present in the hook base to ensure good air circulation.

In the further embodiments illustrated in FIGS. 11 and 12, the strips 11 are connected to each other in an elastic-bendable manner by bridges 18, whereby the bridges 18 are essentially present in the middle of the strips 11. As can be seen in FIG. 12, there are slits 15 or holes 16 in the bridges 18 and/or in the strips 11 to provide good ventilation.

Figure 13:
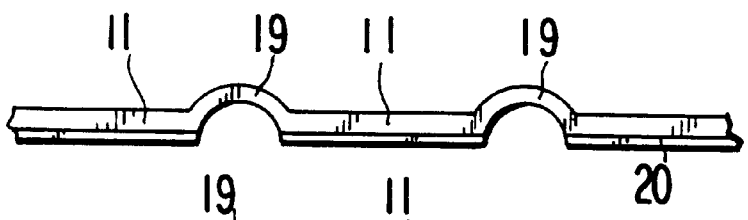
FIG. 13: a partial view in the longitudinal direction of a rolling shell with arch-shaped bridges.
Figure 14:
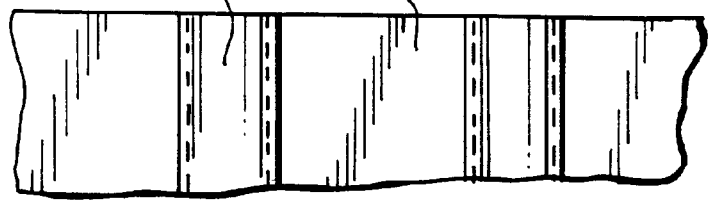
FIG. 14: a plan view of the rolling shell according to FIG. 13.

Finally, FIGS. 13 and 14 show a last embodiment in which externally bowed arches 19 are provided as elastic bridges between the strips 11. These arches 19 particularly allow flexibility in the circumferential direction and, if required, allow rolling up toward the inside, and enhance the longitudinal rigidity in the same way as corrugated iron or corrugated cardboard.

In all embodiments according to FIGS. 6 to 14 it can be seen that a breathable inner lining 20 is applied, e.g. by adhesive, to the strips 11 on the inside of shell 1.

Finally it should be noted that the inventive rolling orthesis can be used in technically the same embodiments but without the shoulder retention cap as an ulnar fracture orthesis (forearm orthesis) and, with a heel cap instead of the shoulder retention cap, as a tibia fracture orthesis (leg orthesis) with just minor alteration of the contours (distal and proximal) of the rolling shell.

What is claimed is:

1. A rolling fracture orthesis, comprising:
a shell that is roll-flexible in a circumferential direction to surround a limb to be supported, the shell having adjacent bend-resistant strips that are pivotably interconnected and arranged parallel to each other in a longitudinal direction;
hook and pile fastener tapes arranged to hold the strips together; and
a breathable, skin-compatible material applied to only an inner side of the strips, the hook and pile fastener tapes being passed completely around an outer circumference of the shell always in a same direction of application.

2. An orthesis according to claim 1, wherein the strips are made from at least one of plastic, wood and metal and are about 9 mm wide and about 3 mm thick.

3. An orthesis according to claim 1, wherein the support material is air-permeable, tear resistant and flexible.

4. An orthesis according to claim 1, wherein the strips are directly joined to each other by joints, each strip having a laterally projecting, at least partially cylindrical joint shaft running longitudinally along one long-thin side of the strip and a cylindrical joint socket running longitudinally along an opposite long-thin side of the strip so that the joint shaft of one strip engages in the joint socket of an adjacent strip so that it is longitudinally displaceable and swivellable but cannot be pulled out in a circumferential direction.

5. An orthesis according to claim 4, wherein the joint shaft is formed as one piece in the longitudinal direction with one of longitudinal ventilation slits and holes.

6. A. An orthesis according to claim 4, wherein the joint shaft is formed of several joint shaft pieces provided at intervals in the longitudinal direction.

7. An orthesis according to claim 4, wherein the strips are made of solid material.

8. An orthesis according to claim 4, wherein the strips are hollow in crosssection and have internal strengthening ribs.

9. An orthesis according to claim 4, wherein the strips are formed from roller-shutter elements, whereby the joint shaft projecting from one thin side is shaped as a joint hook on one strip and engages in a swivellable manner in the joint socket on the thin side of the adjacent strip so that it can be displaced in the longitudinal direction and additionally can move slightly inside the other with some play in one of a tangential and circumferential direction.

10. An orthesis according to claim 1, wherein the strips are joined together by thin flexible bridges of a common material with the strips, at least one of the bridges and the strips having aeration and ventilation openings.

11. An orthesis according to claim 10, wherein the bridges between the strips are short, straight bridges.

12. An orthesis according to claim 10, wherein the bridges between the strips are formed as outwardly bulging arches, whereby the strips exhibit a thickness approximately equal to the arches, whereby a complete unit is formed that is laterally flexible and longitudinally rigid.

13. An orthesis according to claim 1, and further comprising a shoulder retention cap mounted to an outer section of the rolling shell in a positionally adjustable manner.

14. An orthesis according to claim 13, wherein the shoulder retention cap is L-shaped.

15. An orthesis according to claim 13, wherein the shoulder retention cap is formed to match a course of an arm-shoulder outline.

16. An orthesis according to claim 13, wherein the shoulder retention cap, in a mounted state, has a long, vertical guide arm and short, horizontal support arm that run together in an arch-shaped portion.

17. An orthesis according to claim 16, and further comprising a pad mounted on an underside of an outer end of the support arm.

18. An orthesis according to claim 17, wherein the pad is circular.

19. An orthesis according to claim 17, wherein the pad is a strip that runs along the entire arch-shaped portion.

20. An orthesis according to claim 16, wherein the guide arm has a lower end section secured in overlapping fashion on the shell so that the guide arm can be displaced longitudinally and swivel slightly in the vertical/longitudinal directions.

21. An orthesis according to claim 20, wherein two longitudinal guide slots parallel to each other are provided on the lower end section of the guide arm, and further comprising perpendicular bolts arranged to pass through each of the slots and secured in the shell so that a nut can be screwed firmly onto a projecting end of each bolt.

22. An orthesis according to claim 13, wherein the shoulder retention cap is gutter-shaped with a common radius of curvature with the shell in an applied state and is made of the same material as the strips of the rolling shell.

23. An orthesis according to claim 22, wherein the shoulder retention cap is made of waterproof plastic and has ventilation holes therein.

24. An orthesis according to claim 22, wherein the shoulder retention cap is gutter-shaped and is transversely slightly elastic to allow deformation when applying and removing the orthesis.

25. An orthesis according to claim 13, and further comprising a breathable, skin-compatible inner lining fitted on an inner side of the rolling shell, the strips and the cap.

26. An orthesis according to claim 25, wherein the inner lining is one of a textile, a cotton tissue, and a plush lining.

* * * * *